United States Patent [19]
Johnson et al.

[11] Patent Number: 5,735,831
[45] Date of Patent: Apr. 7, 1998

[54] EXPANDABLE FLOWRATE CATHETER ASSEMBLY AND METHOD OF MAKING SAME

[75] Inventors: Kirk Johnson, Miami Lakes; Stephen J. Querns, Boca Raton, both of Fla.

[73] Assignee: Cordis Corporation, Miami Lakes, Fla.

[21] Appl. No.: 677,889

[22] Filed: Jul. 10, 1996

[51] Int. Cl.$^6$ .................................................. A61M 25/00
[52] U.S. Cl. ............................................ 604/280; 604/264
[58] Field of Search ............................. 604/43, 104–6, 604/264, 280, 103, 96; 606/191, 192, 194, 198

[56] References Cited

U.S. PATENT DOCUMENTS

| | | | |
|---|---|---|---|
| 4,501,264 | 2/1985 | Rockey | 604/103 |
| 4,714,460 | 12/1987 | Calderon | 604/264 |
| 4,961,731 | 10/1990 | Bodicky et al. | |
| 5,049,132 | 9/1991 | Shaffer et al. | 604/96 |
| 5,171,223 | 12/1992 | Herzberg | 604/104 |
| 5,213,576 | 5/1993 | Abiuso et al. | 604/96 |
| 5,254,084 | 10/1993 | Geary | 604/280 |
| 5,290,306 | 3/1994 | Trotta et al. | 606/194 |
| 5,509,900 | 4/1996 | Kirkman | 604/280 |
| 5,562,652 | 10/1996 | Davis | 604/264 |
| 5,613,948 | 3/1997 | Avellanet | 606/194 |

*Primary Examiner*—Mark Bockelman
*Assistant Examiner*—Ronald K. Stright, Jr.
*Attorney, Agent, or Firm*—Watts, Hoffman, Fisher & Heinke, Co., L.P.A.

[57] ABSTRACT

A catheter assembly is provided for delivering a diagnostic fluid to a diagnostic site within the vascular system of a patient comprising an elongated central tube that can be routed into and through a vascular system of a patient, the tube including a tube proximal end and a tube distal end, a flexible sleeve defining a space between the interior surface of the sleeve and an exterior surface of the central tube, the sleeve comprising a sleeve proximal end sealably connected to the exterior circumference of the central tube. The sleeve extends along a length of the central tube from the sleeve proximal end to a sleeve distal end, the central tube defining one or more openings that extend through a wall of the central tube so that the interior of the central tube is in fluid communication with the interior of the sleeve.

8 Claims, 3 Drawing Sheets

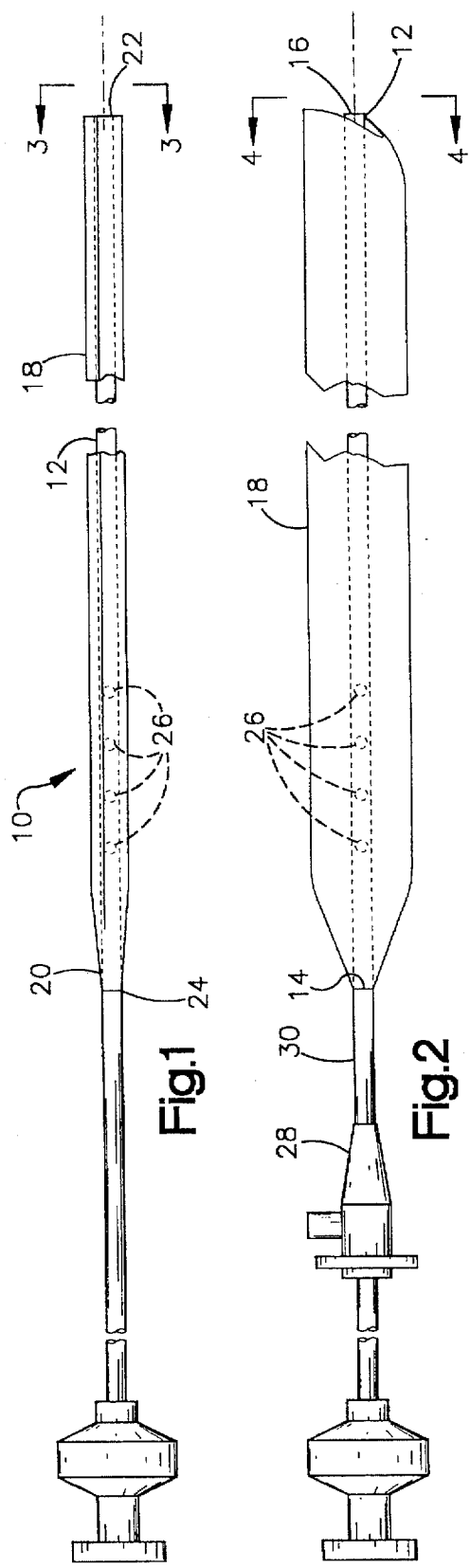
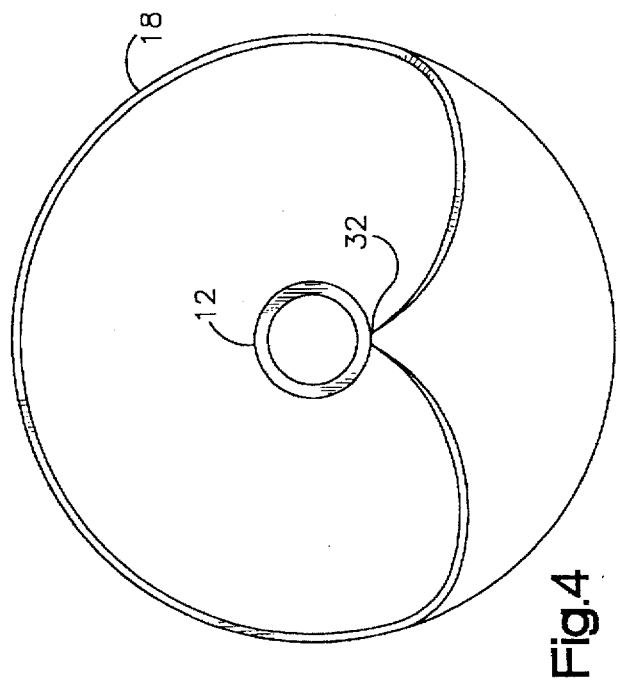
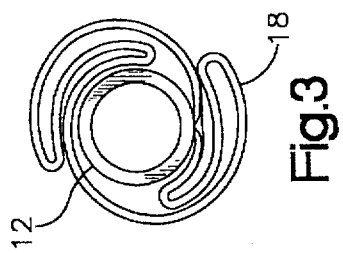

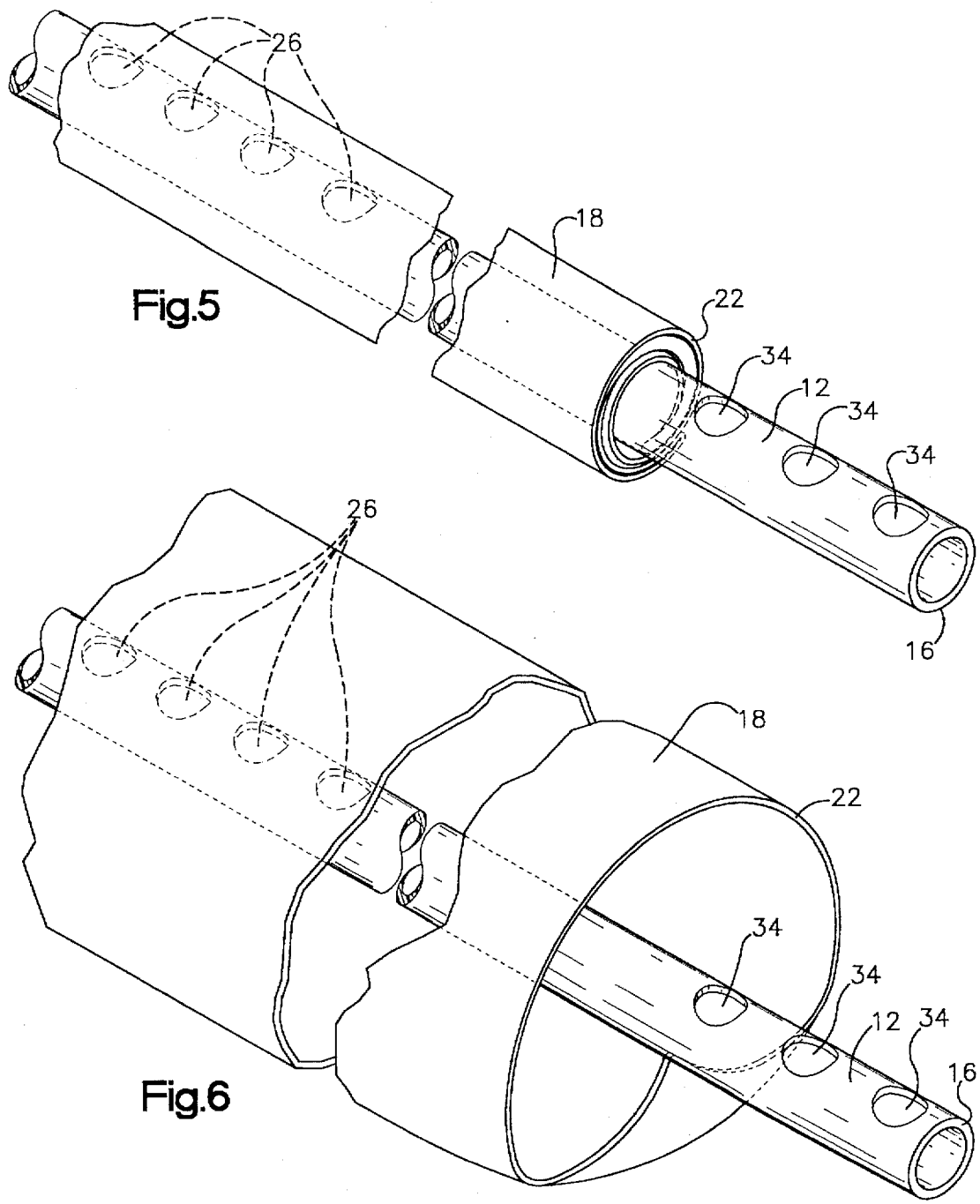

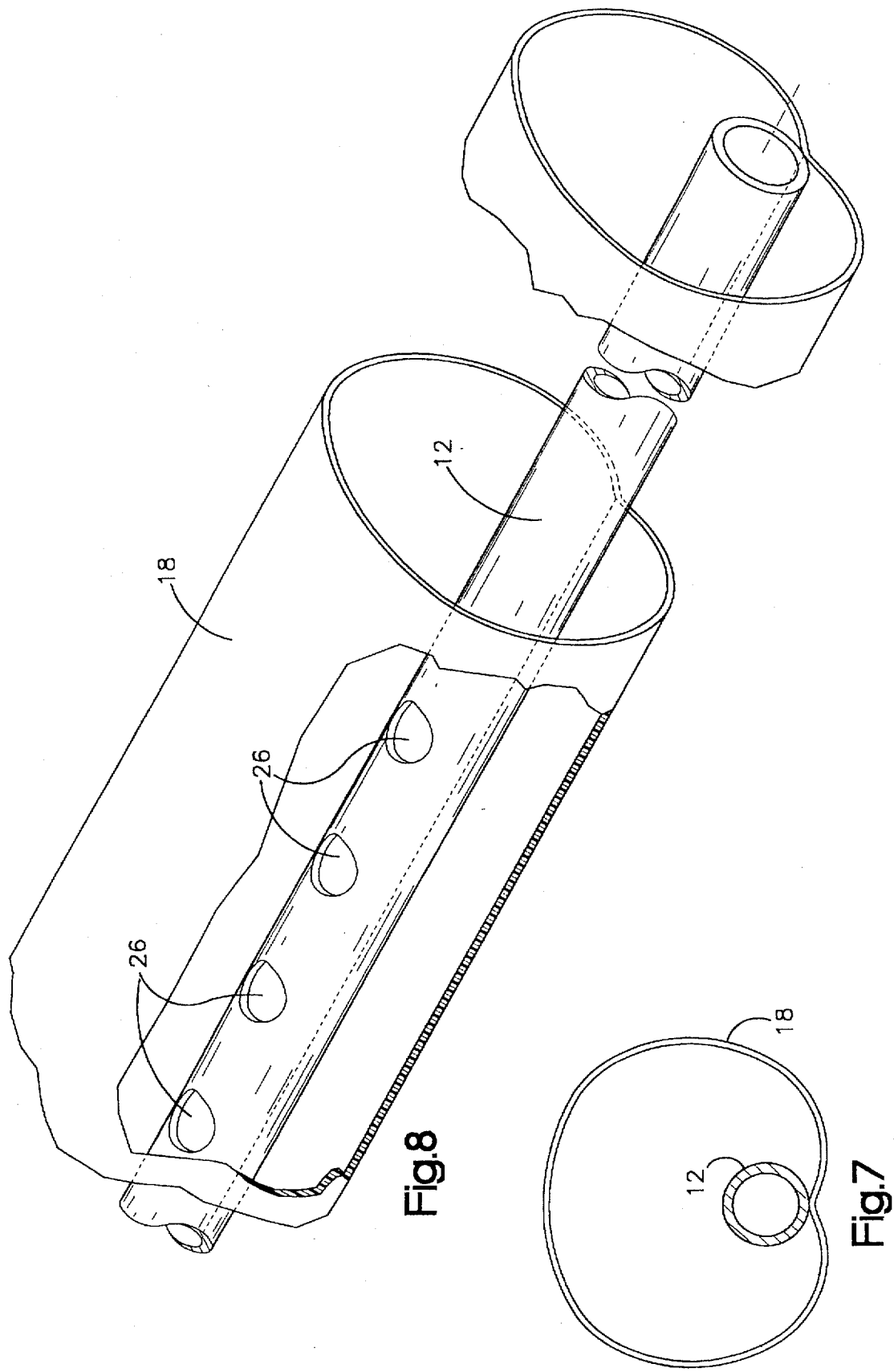

EXPANDABLE FLOWRATE CATHETER ASSEMBLY AND METHOD OF MAKING SAME

FIELD OF THE INVENTION

The present invention concerns a catheter assembly that delivers a diagnostic fluid into a vascular system, and a method of making the assembly.

BACKGROUND ART

Diagnostic or angiographic catheters for introducing a radiopaque dye into a blood vessel for diagnosing a condition of the blood vessel are well known in the prior art. A diagnostic catheter is an elongated flexible member having a passageway for delivering a radiopaque dye under pressure from a source outside the patient to a diagnostic site within a patient. A typical use of such a dye is for imaging a region of the blood vessel on a diagnostic imaging screen.

A typical diagnostic procedure begins with an incision formed in the patient where the diagnostic catheter is to be inserted into an artery. A percutaneous introducer is inserted into the incision to form a passageway into the subject vasculature. The catheter is pushed through the introducer into the vasculature. If only a small diameter catheter is inserted, it is advantageous to use a small introducer so the incision is also small.

In many diagnostic procedures the introducer is inserted into the vasculature of the patient at an access site spaced a significant distance from the intended delivery site for the radiopaque dye. As an example, when conducting a study of blood flow through the heart, the catheter may be inserted into the femoral artery in the groin and routed up the aortic artery over the aortic arch to the region of the heart. Since this insertion technique is a well known technique, specially shaped catheters configured for this procedure are commercially available from a number of sources.

Diagnostic catheters are categorized by their fluid delivery capacity. This capacity is dependent on the cross sectional area of the interior of the catheter available for fluid delivery. A special classification system has been developed to describe catheter size. For example, a french 4 catheter (Fr 4) is a catheter having an outer diameter of approximately 1.32 millimeters, where one french is the equivalent of one-third of a millimeter. Percutaneous introducers are also characterized using this system. The dimension of the introducer referenced using this system is the internal diameter of the introducer passageway through which the catheter passes. Therefore, a french 4 introducer (Fr 4) refers to an introducer with a passageway having an inner diameter of approximately 1.32 millimeters with sufficient tolerance to receive up to a Fr 4 catheter.

Certain diagnostic procedures require high flow rates to produce adequate images. This flow rate requirement for diagnostic catheters limits the ability to reduce the interior cross-sectional area and use a smaller introducer. For example, certain diagnostic procedures require a volume of fluid delivered by a Fr 8 catheter, requiring at a minimum a Fr 8 introducer. It is a goal of the present invention to minimize the size of the incision required to access the patient's vasculature while delivering a volume of diagnostic fluid which has previously required a larger incision and a larger introducer.

Certain procedures also require the deployment of instrumentation or devices, such as stents, in addition to diagnostic fluid. Typically, such instrumentation and devices are deployed through the interior of an elongated flexible member, or guide catheter. Conventional guide catheters must be large enough to accommodate the instrumentation and deliver a sufficient volume of diagnostic fluid through the same passageway. These requirements for traditional guide catheters limit the ability to reduce the interior cross-sectional area of the catheter and use a smaller introducer. It is another goal of the present invention to reduce the size of the guide catheter and the size of the required incision at the access site while delivering a sufficient volume of diagnostic fluid.

SUMMARY OF THE INVENTION

The present invention provides a catheter assembly with a reduced cross sectional profile during insertion that is capable of delivering a volume of diagnostic fluid consistent with a larger diagnostic catheter or a larger guide catheter requiring a larger introducer. The catheter assembly of the present invention allows for a smaller introducer to be used, resulting in a smaller incision at the access site. These advantages are obtained while delivering a volume of diagnostic fluid required for successful imaging of the subject vessel. A catheter assembly within the scope of the present invention can deliver a volume of fluid consistent with a Fr 8 catheter, while only requiring a Fr 4 introducer.

In accordance with the above, the present invention provides for a catheter assembly comprising an elongated central tube that can be routed into and through a vascular system of a patient, having a tube proximal end and a tube distal end, and a flexible sleeve defining a space between the interior surface of the sleeve and an exterior surface of the central tube, having a sleeve proximal end sealably connected to the central tube. The sleeve extends along a length of the central tube from the sleeve proximal end to a sleeve distal end. The central tube defines one or more openings that extend through a wall of the central tube so that the interior of the central tube is in fluid communication with the interior of the sleeve.

In the preferred embodiment the sleeve is tubular and surrounds the length of the central tube. The sleeve distal end and the tube distal end are coplanar. The sleeve is prevented from rolling back from the central tube during insertion through the introducer by connecting the sleeve to the central tube at one or more locations along the length of the sleeve, and preferably at a single location at the sleeve distal end. An alternate embodiment provides for the sleeve to be connected to the central tube along the entire length of the sleeve.

In another embodiment of the present invention, the central tube extends downstream from the sleeve distal end. The area subject to fluid discharge is expanded to include that portion of the vessel downstream from the sleeve distal end as well as that portion of the vessel downstream from the central tube distal end. In still another alternate embodiment, that portion of the central tube extending downstream from the sleeve distal end preferably defines one or more openings that extend through a wall of the central tube so that the interior of the tube is in fluid communication with the interior of the vasculature. The fluid exiting from these central tube openings flows generally perpendicular to fluid exiting the sleeve, enhancing mixing and dispersion of the discharge fluid.

In an alternate embodiment, the central tube is used as a guide catheter to deploy instrumentation or devices. In this embodiment the diameter of the central tube is less than conventional guide catheters, since the central tube need only accommodate the instrumentation or device being deployed, and diagnostic fluid flows primarily through the attached sleeve. The instrumentation or device within the central tube diverts diagnostic fluid through the central tube openings into the sleeve.

In the preferred embodiment, the sleeve is manufactured from nylon. The sleeve is collapsed or folded around the central tube during insertion through the introducer and deployment to the treatment site. The sleeve is set in its collapsed configuration by exposure to heat or pressure, or a combination of heat and pressure as is known in the art. The pressure resulting from the flow of diagnostic fluid through the central tube openings is sufficient to break the set and causes the sleeve to expand.

A method of constructing a catheter assembly in accordance with the present invention comprises the steps of forming an elongated central tube having a proximal end to receive fluid and defining a center lumen, and having a length sufficient to extend from outside a patient through the vascular system of the patient to a site for injection of a diagnostic fluid, sealably connecting a flexible sleeve at a sleeve proximal end to the central tube, the sleeve extending along a length of the central tube to a sleeve distal end and defining a space between the interior surface of the sleeve and an exterior surface of the central tube, providing one or more openings in the wall of the central tube so that the interior of the central tube is in fluid communication with the interior of the sleeve, and collapsing the sleeve about the exterior of the central tube to allow for insertion through an introducer into the vasculature.

One object of this invention is to provide a catheter assembly having a reduced profile during insertion through an introducer that delivers a quantity of diagnostic fluid consistent with a catheter requiring a larger introducer. It is further an object of this invention to provide a catheter for deploying instrumentation or devices and adequate diagnostic fluid with a single insertion procedure. The present invention allows the central tube deploying the instrumentation to be downsized, allowing a smaller introducer to be used.

Further features and advantages of the invention will become apparent from the following detailed description of a preferred embodiment made with reference to the accompanying drawings.

BRIEF DESCRIPTION OF THE DRAWINGS

FIG. 1 is a broken side view of a diagnostic catheter assembly in accordance with the present invention prior to the introduction of diagnostic fluid into the assembly, with the central tube and central tube openings in outline;

FIG. 2 is a broken side view of the diagnostic catheter assembly of FIG. 1 after introduction of diagnostic fluid into the assembly, with the central tube and central tube openings in outline, and further depicting an introducer;

FIG. 3 is an end view of the diagnostic catheter assembly of FIG. 1 as seen approximately from the plane indicated by the line 3—3;

FIG. 4 is an end view of the diagnostic catheter assembly of FIG. 2 as seen approximately from the plane indicated by the line 4—4;

FIG. 5 is a broken perspective view of a second embodiment of a diagnostic catheter assembly constructed in accordance with the present invention prior to introduction of diagnostic fluid into the assembly;

FIG. 6 is a broken perspective view of the embodiment of FIG. 5 after introduction of diagnostic fluid into the assembly;

FIG. 7 is a sectional view of a third embodiment of a catheter assembly constructed in accordance with the present invention, after introduction of diagnostic fluid into the catheter assembly; and FIG. 8 is a broken perspective view of the embodiment of FIG. 7.

DESCRIPTION OF THE PREFERRED EMBODIMENT

A catheter assembly according to the preferred embodiment of the present invention is depicted in FIG. 1 and is generally designated as 10. The assembly includes an elongated central tube 12 with a tube proximal end 14 and a tube distal end 16. A sleeve 18 having a sleeve proximal end 20 and a sleeve distal end 22 is insert molded or heat sealed at the sleeve proximal end 20 to the exterior of the central tube 12 to form a sealed connection 24 between the sleeve proximal end 20 and the exterior circumference of the central tube 12. The sleeve distal end 22 is connected to the central tube 12 at the tube distal end 16. The central tube 12 includes openings 26 extending though the wall of the tube 12 and located between the tube distal end 16 and the sleeve proximal end 20. FIG. 1 shows the catheter assembly 10 prior to introduction of the pressurized diagnostic fluid into the assembly.

The central tube 12 is formed as a conventional diagnostic or guide catheter as is known in the art. Central tube openings 26 through the catheter wall place the interior of the tube 12 in fluid communication with the interior of the sleeve 18.

The collapsed configuration of the sleeve 18 prior to introduction of pressurized diagnostic fluid can better be understood by examining FIG. 3. The collapsed sleeve 18 adds approximately six layers of sleeve wall thickness to the outer diameter of the central tube 12. The sleeve wall of the preferred embodiment has a thickness of about 0.018 min. The collapsed sleeve 18 of the preferred embodiment contributes approximately 0.11 mm. to the overall diameter of the assembly 10 during deployment.

A percutaneous introducer 28 having an opening through which the assembly 10 passes is shown toward the tube proximal end 14 in FIG. 2. FIG. 2 illustrates the embodiment of FIG. 1 after introduction of pressurized diagnostic fluid into the tube proximal end 14. The force provided by the fluid flow through the central tube openings 26 causes the sleeve 18 to unfold, creating an increased area between the interior surface of the sleeve 18 and the exterior surface of the central tube 12 available for fluid flow. It will be appreciated by those skilled in the art that the inner diameter of the sleeve 18 in its unfolded configuration is a matter of choice. In this preferred embodiment, fluid also flows through the central tube 12 and exits the tube distal end 16 into the vasculature at the diagnostic site.

The additional area available for fluid flow once the pressurized diagnostic fluid causes the sleeve 18 to unfold can be seen in FIG. 4. In the preferred embodiment of FIGS. 1 through 4 the sleeve 18 is capable of expanding to approximately 2.64 mm. and achieves this expansion when diagnostic fluid is injected into the tube proximal end 14 at approximately 500 psi. The collapsed sleeve and central tube of the preferred embodiment can be inserted into the vasculature using a Fr 4 introducer with an opening of about 1.32 min. It will be appreciated that the sleeve diameter and length, the fluid injection pressure, the size and number of the central tube openings, and the placement of the central tube openings are factors that will effect the flowrate of diagnostic fluid delivered through the sleeve. The flowrate through the sleeve 18 is maximized by insuring that the sleeve is fully expanded and by positioning the central tube openings 26 just downstream from the sealed connection 24 between the sleeve 18 and the central tube 12. The central tube openings 26 should also be positioned to avoid the introducer sheath 30 typically attached to introducers. The sheath 30 forms a conduit typically less than 25 cm. in length and extending from the introducer into the vasculature, and having the same inner diameter as the introducer.

Additionally, FIG. 4 illustrates the connection 32 of the sleeve 18 to the central tube 12. This connection 32 maintains the relative position of the sleeve 18 and the tube 12 and prevents the sleeve 18 from peeling down the length of the central tube 12 as the assembly 10 is pushed through the introducer 28 and deployed to the diagnostic site. The connection 32 can be made at a single location as depicted in FIGS. 1 through 4, or at more than one location along the length of the sleeve 18.

The preferred embodiment depicted in FIGS. 1 through 4 includes sixteen central tube openings 26, four each on opposing sides of the central tube 12, each opening 26 having a diameter of approximately 0.5 min. The openings 26 commence at a position downstream from the introducer 28 to avoid the sheath 30. This embodiment produces a fluid flow equivalent to using a Fr 8 catheter and a Fr 8 introducer, while only requiring the use of a Fr 4 catheter and a Fr 4 introducer.

According to further aspects of the present invention, the arrangement, size and number of central tube openings 26 and the expanded inner diameter of the sleeve 18 are preselected to permit the desired amount of pressurized fluid to flow into the patient's vessel at the diagnostic site. It will be appreciated that the number, size and arrangement of the central tube openings 26 and the expanded inner diameter of the sleeve 18 are matters of choice and that embodiments varying the number, size and arrangement of the central tube openings 26 and the expanded inner diameter of the sleeve 18 are within the scope of the present invention.

A second embodiment of the catheter assembly 10 of the present invention is depicted in FIGS. 5 and 6. The sleeve distal end 22 is not coplanar with the central tube distal end 16. Rather, the central tube extends downstream from the sleeve distal end 22. As shown in FIG. 6, the pressurized diagnostic fluid has caused the sleeve 18 to unfold away from the central tube 12, creating an additional area available for fluid flow. In this embodiment the diagnostic site subject to fluid discharge is expanded to include portions of the vessel through which the central tube 12 is threaded.

The embodiment of FIGS. 5 and 6 includes central tube openings 34 along that length of the central tube 12 extending downstream from the sleeve distal end 22. These central tube openings 34 provide a fluid discharge generally perpendicular to and coplanar with a portion of the fluid discharge from the sleeve distal end 22. The interference between these fluid discharge patterns enhances mixing and dispersion of the fluid at the diagnostic site.

Central tube openings 34 downstream from the sleeve distal end 22 as depicted in FIGS. 5 and 6 are not required to be included in an expandable flowrate diagnostic catheter assembly in order to fall within the scope of the claimed invention. The embodiment depicted in FIGS. 5 and 6 is useful where fluid discharge is desired in a larger body lumen as well as in a smaller lumen downstream from the sleeve distal end 22. The sleeve 18 provides diagnostic fluid to the larger body lumen, while the central tube 12 provides diagnostic fluid to the smaller downstream body lumen.

A third embodiment of the present invention is depicted in FIGS. 7 and 8. The sleeve 18 is connected to the central tube 12 along the length of the sleeve 18 forming an asymmetrical assembly. It is within the intended scope of the present invention to control the shape of the assembly when the sleeve 18 is expanded by adjusting the connection between the sleeve 18 and the tube 12. As shown in FIGS. 7 and 8, after the diagnostic fluid has been injected into the tube proximal end 14 and through the central tube openings 26, the sleeve 18 unfolds to create an additional space available for fluid flow.

The sleeve material of the preferred embodiment is preferably oriented nylon 12, although other suitable materials capable of flexibly collapsing about the exterior of the central tube without significantly increasing the outer diameter of the catheter assembly can be used for the sleeve material. The sleeve material of the preferred embodiment is capable of setting in its collapsed configuration when exposed to pressure or heat, or a combination of both as is known in the art. The collapsed configuration of the preferred embodiment is achieved by placing the central tube 12 and the collapsed sleeve 18 into a forming tube (not shown). The assembly is then subjected to a standard sterilization procedure. The sleeve 18 maintains its collapsed configuration about the central tube 12 after the forming tube is removed until introduction of the pressurized fluid forces the sleeve 18 to unfold. It will be appreciated that alternate methods of maintaining the sleeve 18 in its collapsed configuration prior to the introduction of pressurized fluid can be utilized without departing from the intended scope of the present invention. By way of example, heat shrink tubing can be wrapped or tied around the collapsed sleeve until the pressurized fluid releases the tubing and allows the sleeve 18 to expand.

Numerous variations and modifications, in addition to those already described herein, will be apparent to those skilled in the art, without departing from the scope of the present invention.

What is claimed is:

1. A catheter assembly for percutaneously delivering diagnostic fluid to a site in the interior of a patient blood vessel comprising:

a) an elongated tube having a center passageway that can be routed into and through a vascular system of a patient, said elongated tube including a tube proximal end and a tube distal end;

b) a flexible sleeve supported by the elongated tube near the tube distal end and defining a space between the interior surface of the sleeve and an exterior surface of said elongated tube, wherein said sleeve comprises a proximal end that is sealed around an exterior circumference of said elongated tube, and wherein said sleeve extends along a length of said elongated tube from said proximal end to a sleeve distal end, and wherein said sleeve distal end defines a generally annular diagnostic fluid delivery opening about an outer surface of said elongated tube through which fluid flows out of said sleeve into the blood vessel; and c) said tube defining one or more tube openings that extend through a wall of said tube so that the passageway of the elongated tube is in fluid communication with the interior of the sleeve for delivering diagnostic fluid through the one or more tube openings to cause the diagnostic fluid to flow away from the proximal end of the sleeve into the blood vessel through the generally annular fluid delivery opening of said sleeve.

2. The catheter assembly of claim 1 wherein said sleeve is connected to said elongated tube at one or more locations along the length of said sleeve.

3. The catheter assembly of claim 2 wherein said sleeve is connected to said elongated tube at said sleeve distal end.

4. The catheter assembly of claim 1 wherein said elongated tube extends downstream from said sleeve distal end.

5. The catheter assembly of claim 4 wherein said elongated tube defines one or more openings extending through a wall of said elongated tube in that portion of said elongated tube that extends downstream from said sleeve distal end so that the interior of said elongated tube is in fluid communication with the exterior of said elongated tube.

6. The catheter assembly of claim 1 wherein said sleeve is tubular and surrounds a length of said elongated tube.

7. The catheter assembly of claim 1 wherein said sleeve is connected to said elongated tube along a longitudinal length of said sleeve.

8. The catheter assembly of claim 1 wherein the sleeve is manufactured from nylon.

* * * * *